(12) United States Patent
Keane

(10) Patent No.: US 6,632,223 B1
(45) Date of Patent: Oct. 14, 2003

(54) PULMONARY VEIN ABLATION STENT AND METHOD

(75) Inventor: David Keane, Wellesley, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/539,056

(22) Filed: Mar. 30, 2000

(51) Int. Cl.$^7$ .............................................. A61B 18/18
(52) U.S. Cl. .............................. 606/41; 606/7; 606/14; 606/45; 607/88; 607/112; 607/113; 607/116; 604/14; 604/16; 604/507; 623/1.1; 623/1.11; 623/1.12; 623/1.18
(58) Field of Search ................................ 606/7, 13–16, 606/41, 45, 46, 49, 192; 607/88, 92, 116, 112, 113; 128/898; 604/14–16, 507; 623/1.1–1.12, 1.18

(56) References Cited

U.S. PATENT DOCUMENTS

| | | | | |
|---|---|---|---|---|
| 4,580,568 A | * | 4/1986 | Gianturco | 128/345 |
| 4,830,003 A | * | 5/1989 | Wolf et al. | 128/343 |
| 5,078,736 A | * | 1/1992 | Behl | 623/1 |
| 5,100,429 A | * | 3/1992 | Sinofsky et al. | 606/195 |
| 5,156,151 A | | 10/1992 | Imran | 128/642 |
| 5,239,999 A | | 8/1993 | Imran | 128/642 |
| 5,279,299 A | | 1/1994 | Imran | 128/642 |
| 5,281,218 A | | 1/1994 | Imran | 606/41 |
| 5,302,168 A | * | 4/1994 | Hess | 606/3 |
| 5,403,311 A | | 4/1995 | Abele et al. | 606/49 |
| 5,404,638 A | | 4/1995 | Imran | 29/884 |
| 5,406,946 A | | 4/1995 | Imran | 128/642 |
| 5,411,466 A | * | 5/1995 | Hess | 606/3 |
| 5,431,168 A | | 7/1995 | Webster, Jr. | 128/658 |
| 5,476,495 A | | 12/1995 | Kordis et al. | 607/122 |
| 5,484,384 A | | 1/1996 | Fearnot | 600/3 |
| 5,507,743 A | | 4/1996 | Edwards et al. | 606/41 |
| 4,655,771 A | * | 9/1996 | Wallsten | 623/1 |
| 5,573,531 A | | 11/1996 | Gregory | 606/14 |
| 5,582,609 A | | 12/1996 | Swanson et al. | |
| 5,593,405 A | | 1/1997 | Osypka | 606/15 |
| 5,617,854 A | | 4/1997 | Munsif | 128/642 |
| 5,738,683 A | | 4/1998 | Osypka | 606/47 |
| 5,782,899 A | * | 7/1998 | Imran | 607/122 |
| 5,807,306 A | | 9/1998 | Shapland et al. | 604/21 |
| 5,807,395 A | | 9/1998 | Mulier et al. | 606/41 |
| 5,814,039 A | * | 9/1998 | Prescott | 606/7 |
| 5,836,940 A | | 11/1998 | Gregory | 606/15 |
| 5,878,751 A | * | 3/1999 | Hussein et al. | 128/898 |

(List continued on next page.)

FOREIGN PATENT DOCUMENTS

| | | | |
|---|---|---|---|
| EP | 0 626 153 | 11/1994 | |
| WO | WO 0042934 | 7/2000 | A61B/18/14 |

Primary Examiner—Linda C. M. Dvorak
Assistant Examiner—A. Farah
(74) Attorney, Agent, or Firm—Nutter, McClennen & Fish LLP

(57) ABSTRACT

A system for treating atrial fibrillation includes a stent and a delivery catheter for carrying the stent to a treatment site. The stent is self-expanding, for example, being formed of a shape memory alloy, and is configured to lodge against the interior wall of a pulmonary vein. The stent may be formed as a loop, helix, progressively wound helix or other suitable shape, and in one embodiment has an exposed proximal portion including an ablation region that contacts and subtends a circumference of the vein, or contacts endocardial wall tissue along a circumferential path at the ostium. The proximal portion is attached to an energy delivery line in the catheter to energize the stent and ablate tissue in the circumferential region, forming a lesion to block conduction across the ostium or preventing trigger signals originating in the pulmonary vein from initiating or sustaining fibrillation in the atrium. The stent also provides support for the vessel wall, reducing the likelihood of developing pulmonary vein stenosis. The stent may also be deployed without concurrent or concomitant ablation, to prevent or treat primary or secondary pulmonary vein stenosis.

6 Claims, 5 Drawing Sheets

U.S. PATENT DOCUMENTS

| | | | | |
|---|---|---|---|---|
| 5,891,133 A | * | 4/1999 | Marphy-Chutorian | 606/7 |
| 5,895,398 A | | 4/1999 | Wensel | 606/159 |
| 5,980,563 A | * | 11/1999 | Tu et al. | 607/113 |
| 6,012,457 A | | 1/2000 | Lesh | 128/898 |
| 6,024,740 A | * | 2/2000 | Lesh et al. | 606/34 |
| 6,102,908 A | * | 8/2000 | Tue et al. | 606/41 |
| 6,290,696 B1 | * | 9/2001 | Lafontaine | 606/21 |

\* cited by examiner

PULMONARY VEIN ABLATION STENT AND METHOD

CROSS-REFERENCE TO RELATED APPLICATIONS

This application is related to U.S. patent application Ser. No. 09/396,959 filed by applicant on Sep. 15, 1999 for a Coiled Ablation Catheter.

STATEMENT REGARDING FEDERALLY SPONSORED RESEARCH

Not Applicable

BACKGROUND OF THE INVENTION

The present invention relates to cardiac treatment, and particularly relates to methods and devices for treating cardiac conditions such as atrial fibrillation.

Atrial fibrillation is a common cardiac rhythm disorder which can affect the quality of a patient's life and may be associated with significant morbidity. Atrial fibrillation is characterized by a rapid disorganized rhythm of the upper chambers of the heart (the atria). Instead of a single wavefront of electrical activation during regular rhythm, atria fibrillation consists of multiple coexistent wavefronts with random reentry. The condition may arise following cardiac surgery, or after infection. Its etiology is varied and has even been hypothesized in some cases to have a genetic component. While medication is effective to control fibrillation in some patients, endocardial ablation or surgical intervention is often necessary for effective treatment.

Endovascular approaches may be used to create lesions using an ablation catheter to block intraatrial conduction. Surgical procedures such as Cox's maze have been used to address the problem. This procedure creates surgical lines to compartmentalize the tissue of the cardiac wall into a plurality of regions which are each too small to support a depolarization/repolarization cycle.

The results of early clinical trials of ablation to treat atrial fibrillation indicate that in a significant proportion of patients with atrial fibrillation, the cause lies in the pulmonary veins. The pulmonary veins contain a sleeve of heart muscle in their proximal extension from the left atrium, and episodes of atrial fibrillation are often triggered by rapidly discharging foci in this region of the pulmonary veins. Such rapidly discharging foci may be located as far as several centimeters up a pulmonary vein. Catheter ablation of focal triggers in the pulmonary veins has been reported to prevent the recurrence of atrial fibrillation in some patients.

This suggests that rather than attempting to localize sparsely scattered groups of rapidly depolarizing cells, these triggers may be blocked by creating a circumferential lesion at the os of the pulmonary vein, thus simply electrically isolating the entire pulmonary vein from the atrium. Indeed, where a trigger from a venous focus is necessary to initiate or maintain fibrillation, such a circumferential lesion may be all that is required for successful ablation treatment in a significant proportion of patients.

However, clinical case reports indicate that the application of RF energy within the pulmonary veins may be associated with a risk of developing stenosis subsequent to the ablation. This stenosis can result in pulmonary hypertension, requiring a follow-up pulmonary vein balloon angioplasty or other intervention for its resolution.

Thus, treatment of atrial fibrillation in this set of patients by extracardiac ablation may require close follow up and secondary treatment to avoid complications.

It would therefore be desirable to provide a non-surgical treatment for atrial fibrillation.

It would further be desirable to provide a non-surgical treatment without stenotic complications.

SUMMARY OF THE INVENTION

This is achieved in accordance with the present invention by inserting a self-expanding stent configured to lodge in a pulmonary vein and having an exposed conductive region forming a loop. The stent is delivered via a flexibly deflectable endovascular delivery catheter, which is inserted in a femoral vein and follows a transseptal path to carry the stent in a compact form through the left atrium and deliver it to the pulmonary vein. The stent is then at least partially released or ejected from the catheter and expands into position such that the exposed conductive loop contacts the pulmonary vein around the vessel's interior circumference. The stent remains electrically attached to the catheter, which carries an energy supply line, such as an RF cable or other energy conductor, or a cryogenic system, for supplying ablation energy or cryothermy to the stent. This line is then energized to form a lesion in that portion of the vessel contacting the exposed loop, after which the stent is detached from the catheter and remains positioned in the vein to maintain vessel patency. In alternative embodiments, the ablation potion may include a proximal loop sized and positioned to contact the posterior left atrial wall outside the os of the pulmonary vein and ablate a blocking lesion in the wall.

In one embodiment, the stent has the shape of a simple wire or ribbon helix with one or more full circumferential turns or windings of the helix exposed to operate as an ablation electrode and form the ablation lesion. The remaining turns of the helix may be covered by electrical insulation, so that the ablation energy is selectively placed in a circumferential line or band at the os. In another embodiment, the coil forms a closed loop which zig-zags around a ring-like contour such that when expanded it subtends a circumferential cylindrical band around the axis of the vessel. In yet another embodiment, the stent has a proximal coil or loop that is larger than, or expandable to be larger than, the distal portion of its body, which may be formed of coils, loops or other know stenting structures. The proximal portion lies against the endocardial surface of the posterior left atrium, while the distal portion anchors the stent within the pulmonary vein. In this embodiment the proximal portion may be configured to ablate a circumferential lesion outside the pulmonary vein, which may further reduce the risk of inducing pulmonary vein stenosis. Other known stent shapes and structures may be used, which contain, or which are augmented to contain, or which are selectively insulated so as to expose or leave exposed, a conductive loop positioned for defining a blocking lesion at the vessel entrance.

The stent may also be used to prevent or treat pulmonary vein stenosis following ablation of the pulmonary vein or adjacent atrium by any other form of ablative energy system, such as cryothermy, laser, ultrasound, microwave or rf energy treatment, among others. In that case, the proximal portion expands to a size larger than the pulmonary vein os.

The stent may be formed of a material such. as a shape memory alloy (e.g.. nitinol wire or a titanium or other such alloy), or such as a superelastic alloy. The wire or structural material of the stent may, moreover, be of light construction since it need only possess sufficient structural resilient force to counteract venous recoil and prevent stenosis.

In general, applicant contemplates that the ablation energy utilized in a stent of the present invention may take several forms. A radio-frequency signal may be applied to an exposed conductor, and optionally irrigation through the conductor or via an ancillary structure, may be provided to cool the surface, vary electrical conduction or otherwise modulate the lesion characteristics. Alternatively, with suitable stent and delivery structures, ablation may be effected by laser, ultrasound, microwave or cryothermal ablation. For clarity of exposition below, however, the illustrated structures shall be generally described and referred to simply as rf or electrical ablation structures.

Advantageously, the catheter need carry no balloon or other expansion mechanism, and does not actively effect stent expansion, so the delivery system can be quite small. It thus avoids the risk of balloon injury to the venous wall, and avoids the transient pulmonary vein occlusion that occurs with balloon delivery systems. Once deployed, however, the stent may be further expanded, or an anchor mechanism may be set, by balloon inflation if necessary. The electrical connection between catheter and stent may be effected by a fusible link, by a removable ribbon or wire attached with conductive adhesive, or by temporary capture of the stent between, or electrical contact with, conductive components of the stent delivery mechanism.

Once placed, the stent functions as a wall support in the pulmonary vein and thus may reduce wall stress and stretching that occurs, for example, in the presence of left ventricular diastolic dysfunction, mitral stenosis or regurgitation, or other conditions of left atrial hypertension. This further therapeutic support is therefore believed to contribute generally to the integrity of the vessel wall and the health of the subtended lung, and remove a potential contribution to the development of automaticity in the pulmonary vein myocytes.

BRIEF DESCRIPTION OF THE DRAWINGS

These and other features of the invention will be understood from the description below taken in conjunction with the illustrative drawings of representative embodiments, wherein.

DETAILED DESCRIPTION

Figure 1:
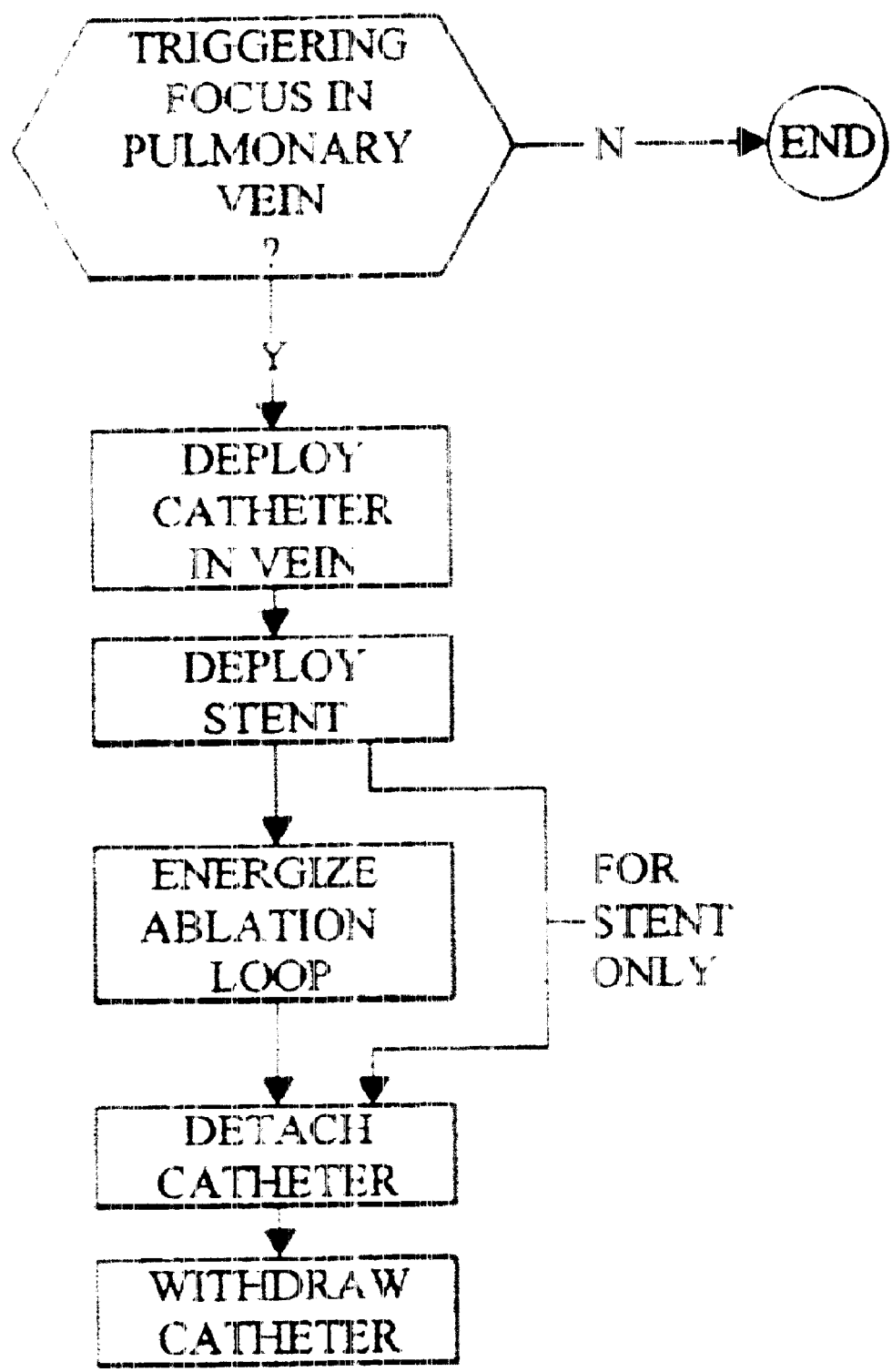
FIG. 1 is a flow chart illustrating steps of the treatment procedure of the present invention.
Figure 1A:
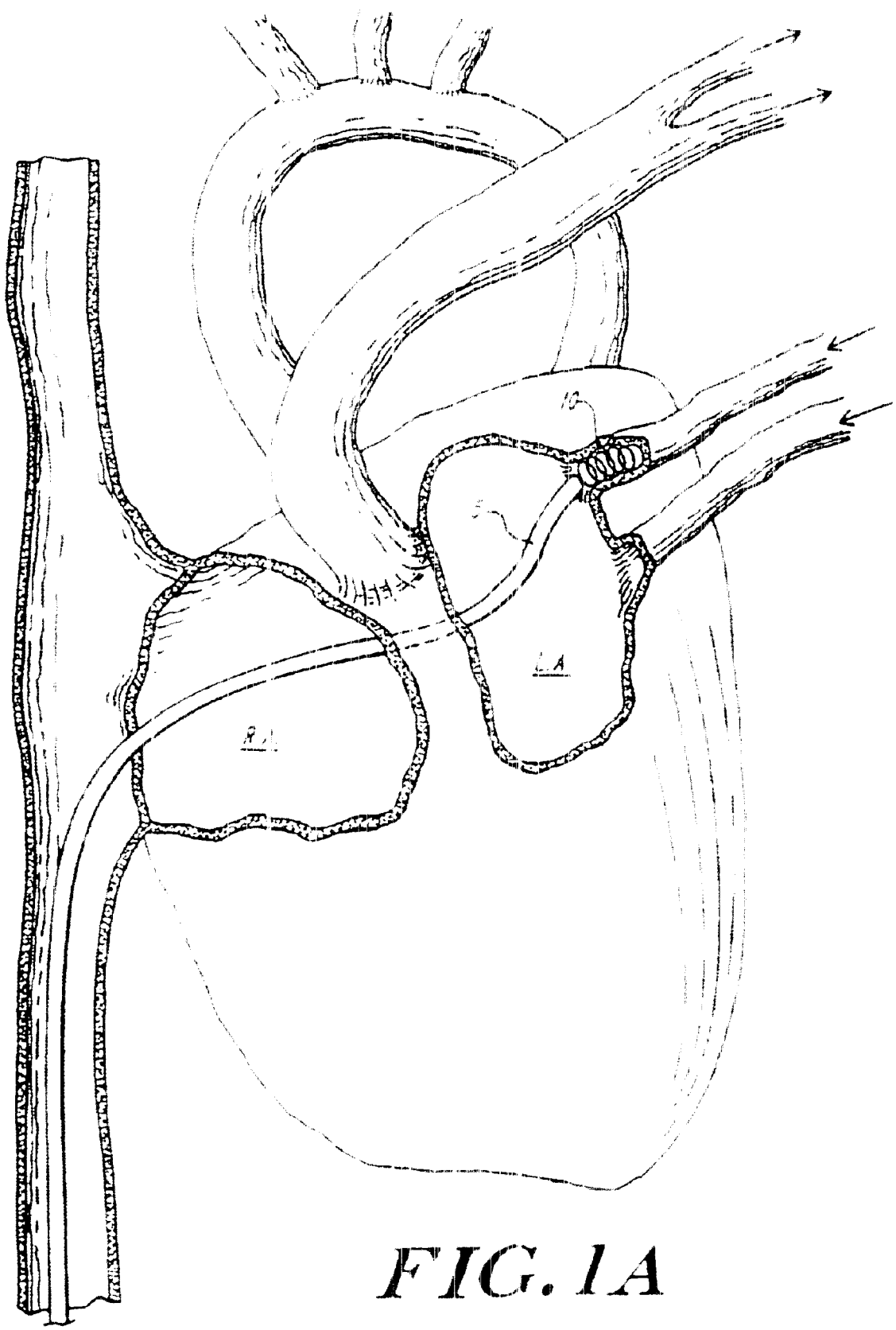
FIG. 1A illustrates catheter placement of the ablation stent in a pulmonary vein.

FIG. 1 illustrates basic steps in a method in accordance with the present invention. The method is broadly applicable to block occult trigger signals from reaching the cardiac wall and is applied when one has, as an initial matter, determined that an arrhythmia is initiated or sustained by triggering signals located in a pulmonary vein. In accordance with the method, a special catheter configured to deliver a stent is employed to access the pulmonary vein. In a typical procedure, the catheter is inserted percutaneously to the femoral vein and navigated along the venous system to the right atrium of the heart, through the atrial septum and into the left atrium. In general, the catheter may be of any suitable design which is sufficiently steerable or deflectable for transseptal access and use. The insertion procedure may involve a preliminary procedure for inserting a guide wire, penetrating the atrial septum and positioning the guide wire to guide the catheter to the intended locus. The catheter is then guided, for example to one of the pulmonary veins in the left atrium, and with its tip positioned just past the ostium is actuated to deploy the stent carried in the catheter tip at a proximal site within the pulmonary vein. Ablation energy is then provided to form a blocking lesion.

Figure 2:
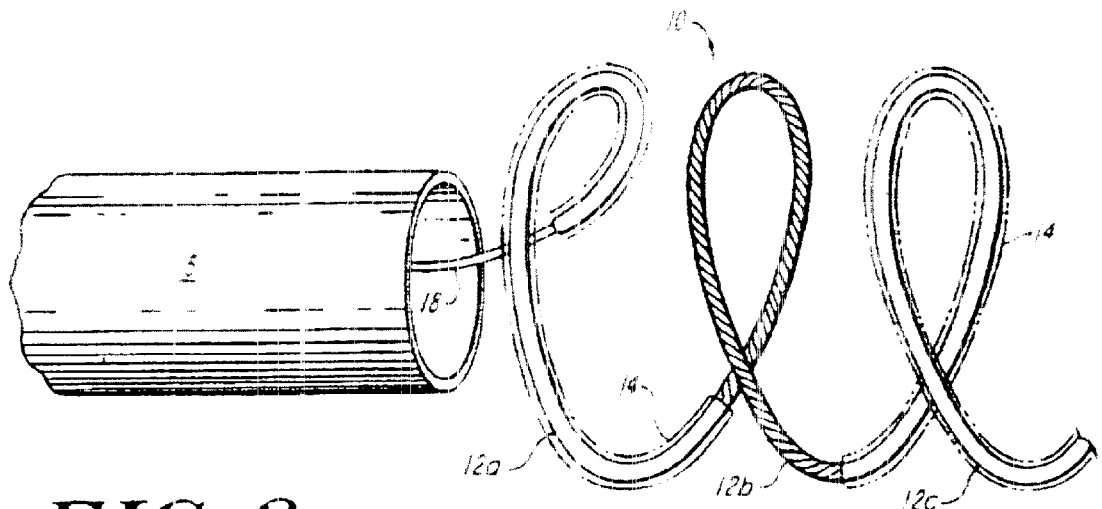
FIG. 2 illustrates a pulmonary vein ablation stent delivery catheter in accordance with one embodiment of the invention.

FIG. 2 illustrates in schematic form the stent and the catheter tip of one system in accordance with the present invention. As shown, the stent 10 is carried within the catheter 5 and is ejected at the time of deployment such that it self-expands to a contour generally larger than that in its stored state, and large enough to exert an outward elastic retaining and supporting force against the wall of the vessel in which it is placed. The illustrated stent 10 is shown as a simple helical winding of diameter larger than the intended vessel inner diameter. Such a stent may be formed of a superelastic material that springs back to a greatly expanded shape, or may be formed of a shape memory alloy (SMA) which reassumes a pre-set larger shape as microstructure of its material composition changes state. Suitable shape memory alloys include Nitinol and various titanium alloys, for which the properties may be varied by suitable selection of the alloy components in a manner known in the art. In general, the shape of the stent is subject to two constraints, namely that it be self-expanding to form a self-anchoring venous stent when deployed, and that it contain an ablation portion, such as an exposed conductive portion, effective to ablate a blocking line in the vessel at or near the os. Preferably this conductive loop or ablation portion, discussed further below, is located at the proximal end, so that any extreme current or heating of the stent is restricted to a small initial length that does not contribute substantially to the overall function of supporting the vessel wall. The proximal location assures that the lesion formed by the stent will block substantially all trigger signals originating in the vein. The stent alloy or material may be selected to be compatible with operation at the ablation temperature, or the exposed ablation band may be implemented with a hybrid structure, by a construction with a suitable conductor separately carried by the self-expanding stent.

As shown in FIG. 2, the illustrated stent 10 includes a number of circumferential windings 12a, 12b, 12c . . . . At least one winding, illustratively winding 12b, is located close to the proximal end of the stent and has an exposed conductive surface that directly contacts the surrounding inner wall of the vessel. Other windings illustratively 12a, 12c have insulating material 14 thereabout. Delivery of the stent from the catheter tip and its deployment in the pulmonary vein may be accomplished by any of a number of known mechanisms, such as by having the stent tightly wound or compacted within an outer sheath that is withdrawn to release the stent for radial expansion; or by having a cylindrical sleeve and an inner plunger within the catheter tip that pushes the stent outwardly therefrom, or grips the stent distal end and pulls it, to deploy it in the vessel. However, whichever ejection or deployment mechanism is utilized, the tip assembly further includes a means for energizing the stent after such deployment.

As further shown in FIG. 2, the proximal end of stent 10 when initially deployed from the tip remains close to or within the catheter. In accordance with a principal aspect of this embodiment of the present invention, this end of the stent is electrically connected to an energy delivery line 18 such as an electrically conductive lead, wire or cable that is energized with a suitable RF or other electrical signal. Continuing with a description of FIG. 1, after the stent is deployed near the ostium of the pulmonary vein, this RF line is activated so that the conductive loop 12b (FIG. 2) contacting the vessel interior ablates a blocking lesion in an arc around the inner vessel wall along its line of contact between the vessel wall and the exposed stent. The stent is then disconnected from the catheter so that it resides as a separate stent remaining in the pulmonary vessel, and the catheter is withdrawn from the patient.

In general, the manner of forming an electrical connection between the energy supply line 18 and the stent 10 may take several forms. One suitable mechanism for connecting the stent and delivery line is to form a fusible link at the junction of the delivery line 18 and the stent 10, with the link having a composition and size that is intended to pass sufficient current for ablating the inner vessel wall, yet to fuse when a short pulse of higher current is applied, thereby causing the two conductive structures to separate. A ground shunt wire within the catheter may be provided to momentarily contact a conductor and cause the link to fuse. Another suitable method of connecting the energy line to the stent is to provide a conductive cylinder or piston at the catheter distal tip which operates as the stent ejection mechanism and which is also connected to the energy supply line. This mechanism captures the proximal end of the stent between or against a structure such as the surrounding sleeve or catheter body (not numbered). The stent then remains electrically connected to the energy source so long as a portion of the distal stent end has not been fully ejected from the catheter. Once the ablation energy has been applied, the cylinder or piston is then advanced (or retracted) to the end of its travel to release the stent entirely and electrically disconnect it. Still a third suitable method of connection is to provide a pigtail connection that may be broken off or severed, or is attached by conductive adhesive and may be peeled back by a simple low-tension pull. Conductive gel or the like may also be used to effect or improve a temporary conductive coupling between parts of the tip assembly and the stent.

Figure 3:
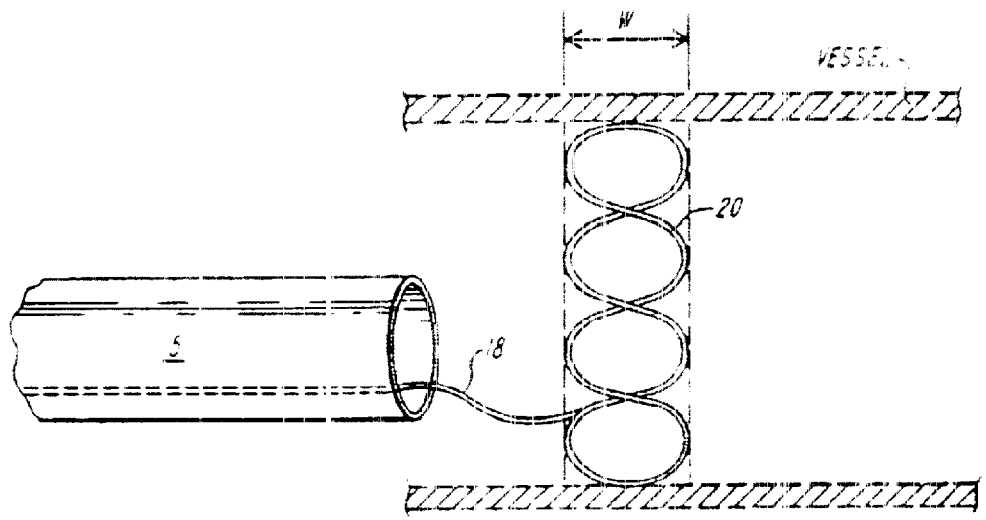
FIG. 3 illustrates a second embodiment of the pulmonary vein ablation stent.

The stent of FIG. 2 is a simple open helical coil. However, applicant contemplates that other forms of expandable or self-expanding stent may be employed or adapted for the intended application. The shape of the stent may take any of a number of forms, such as a serpentine wire or ribbon configuration, a bent-corner zig-zag configuration or other coil configuration compatible with SMA or superelastic expansion or re-shaping for deployment. Thus, for example, a stent may be formed in a closed loop that extends in a narrow zigzag band around a generally circumferential direction as illustrated in FIG. 3 in a side view. As shown in that Figure, the stent 20 is formed of a single strand of material which zig-zags back and forth over a width W in the axial direction, and forms a closed loop so as to provide a springy structure which self-expands to a much greater diameter and provides radial support of the vessel wall. In this case, the entire stent length may operate as an exposed conductor ablation wire. As with the embodiment of FIG. 2, a superelastic or shape memory alloy material may be employed to form the stent and cause it to self-expand without requiring a balloon or other external source of pressure or mechanical expansion force.

In general, applicant contemplates that the self-expanding stent have sufficient outwardly directed force to resist the elastic recoil of the vein, which is rather small in magnitude, and to guard against stenotic narrowing of the vessel following ablation. The ablative operation of the stent may be essentially a unipolar ablation, and carried out by applying RF energy to the conductive contacting portion of the stent while, for example, providing a return path through a large area surface electrode or ground electrode located on the patient's skin. The ground electrode may be positioned so as to minimize the possibility of current paths extending through the heart itself. Alternatively, the ablating loop may carry multiple electrode elements to allow either unipolar or bipolar RF energy delivery as well as cardiac signal recording.

Figure 4:
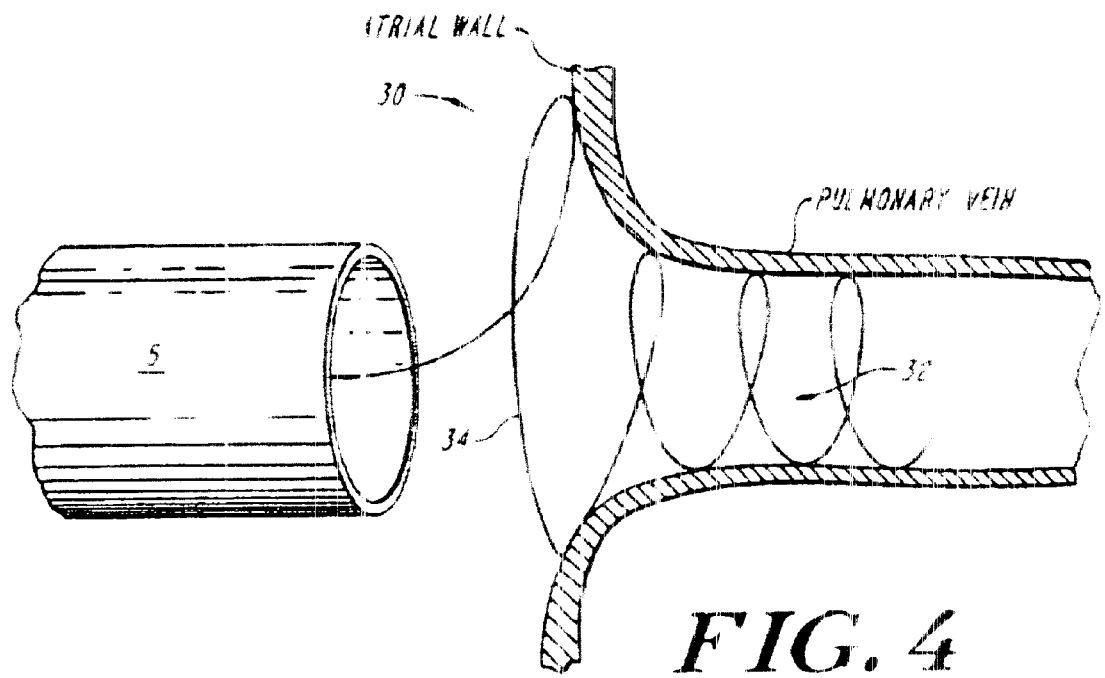
FIGS. 4, and 4A–C illustrate a third embodiment of the stent and a method of deployment.

FIG. 4 shows a third embodiment 30 of the pulmonary vein stent of the present invention configured for delivery by a catheter 5. In this embodiment, the proximal portion of the stent 30 includes a loop 34 that is substantially larger in diameter than the pulmonary vein and remains outside the vein, and a distal portion 32 that extends into and anchors within the vein. In this embodiment, the proximal portion may be the ablation portion, deployed to lie against the endocardial surface of the posterior left atrium and ablate a circumferential lesion outside of and entirely surrounding the pulmonary vein os.

Figure 4D:
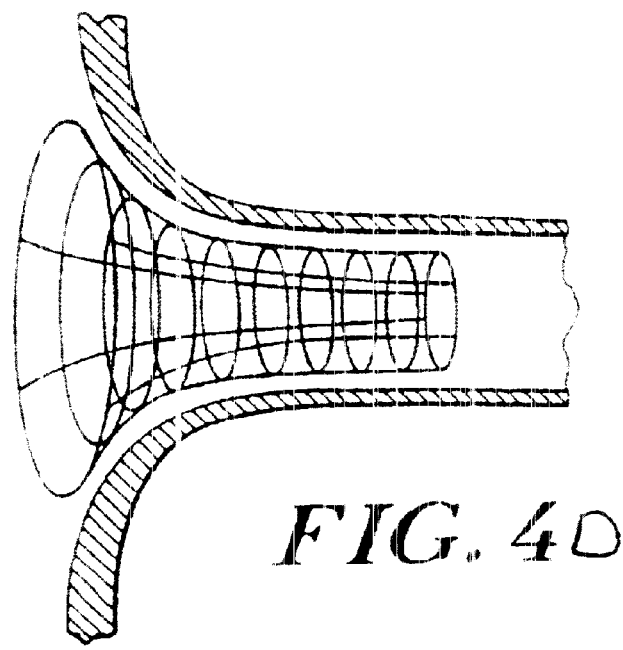
FIG. 4D illustrates another stent embodiment.
Figure 4A:
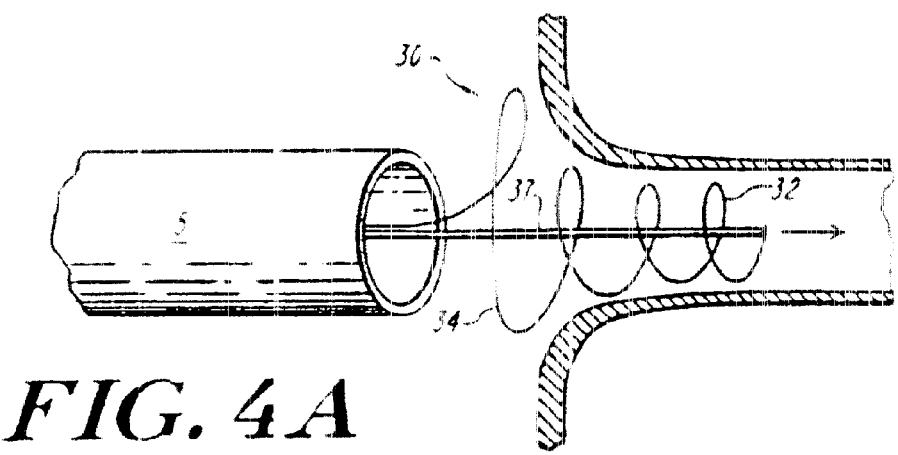
Figure 4B:
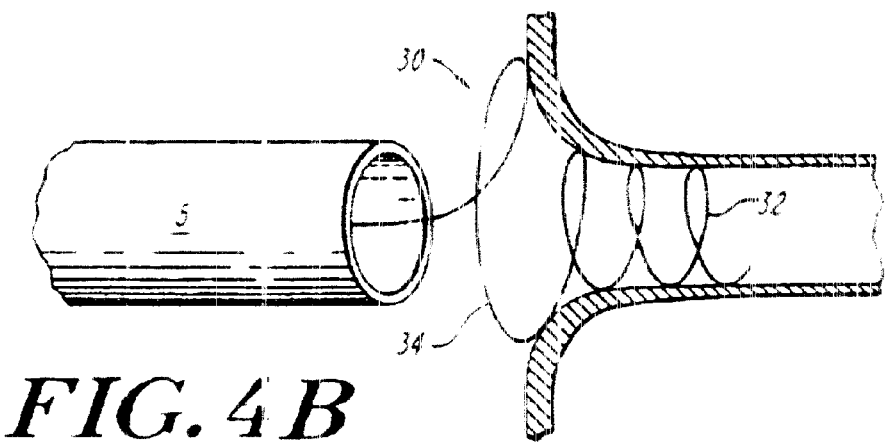
Figure 4C:
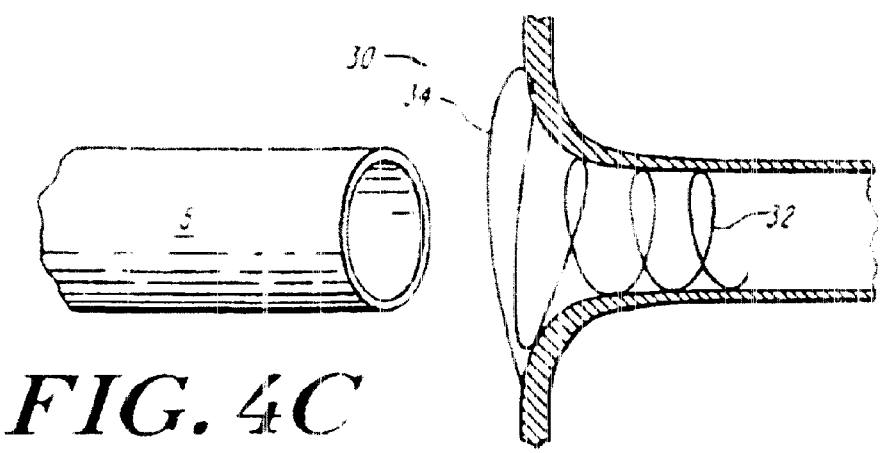

FIGS. 4A–4C illustrate installation and operation of this stent with one delivery catheter 5. As illustrated, the stent 30 may be delivered by a catheter delivery system wherein an axially-moved member 37 engages the distal end 32 of the stent and advances to pull the coiled stent into the pulmonary vein, while the proximal loop 34 remains connected via a catheter 5 to a source of ablation energy. This tensile pulling may reduce the diameter of the coils 32, allowing clearance for the stent to travel up the pulmonary vein to an anchoring site. As shown in FIG. 4B, the puller is then disengaged and may be retracted into the catheter, while the proximal loop 34 elastically bears against the endocardial surface of the posterior left atrium along a path that substantially surrounds the os, while remaining connected to the ablation energy source by connecting portion 38. Once the blocking lesion is formed, the stent is entirely disconnected and left in place, as shown in FIG. 4C.

In this embodiment, preferably the proximal loop 34 is configured to apply the ablation energy, while the distal portion 32 operates as a stent to anchor the assembly and prevent stenosis. The ablation lesion, corresponding to position of the proximal loop or loops 34 in FIG. 4C is thus entirely outside the pulmonary vein. In alternate embodiments, both the distal and proximal portions may be energized. A stent shaped as in FIG. 4 may also be constructed, or used, as a pulmonary vein stent without ablation, to assure patency of the vessel after treatment or ablation has been effected with some other or a conventional ablation catheter. Such a stent may be implemented with spaced-apart loops rather than a helical structure, and may include longitudinal struts to provide further wall support and prevent intercoil recoil, as shown in FIG. 4D.

In addition to the illustrated forms of stent, various other forms of stent either proposed in the literature or existing as commercial products may be readily adapted for the practice of the present invention, and in this case the electrical driving current or other ablation energy and the delivery mechanisms may be modified as appropriate for allowing deployment while connected, and then severing the catheter ablation energy connection. Stents such as flexstent-type, wallstent-type, Gianturco-type stents or Palmaz-type stents may be constructed and configured for the practice of the invention by applying insulation over the distal ends and providing an energy connection in the tip assembly. An expansion balloon may be further provided if needed, dimensions permitting, and the stent itself may be configured with projecting barbs, or treated to assure effective anchoring.

Known RF and other ablation consoles may be adjusted or programmed to apply suitable levels of RF ablation or treatment energy through the exposed portion of the stent. When adapting such existing stents, whether proposed or commercially available, one may change their mechanical properties, and the relative widths or form, to achieve suitable ablation contact areas for use with RF consoles in the practice of the invention, and impedance matching elements may be employed to more closely achieve the desired circuit characteristics for the described ablation procedure. Moreover, it will be appreciated that the conductive portions (12b in FIG. 2, 34 in FIG. 4 or the entire stent in FIG. 3) need not entirely circumscribe the vessel, but are preferably to extend substantially entirely around a full arc and define a blocking lesion of a contour that effectively isolates the distal vessel wall from conduction to and across the ostium into the atrial wall. In this regard, the spiral configuration of the stent shown in FIG. 2 may not entirely disconnect the vessel from the cardiac wall, but may leave a narrow region between successive turns in which, although signals may still be propagated, the length and geometry of the unblocked region effectively prevents trigger signal leakage to the heart. The embodiment of FIG. 3 on the other hand forms a completely circumferential blocking lesion, and that of FIG. 4 may employ partial or multiple turns in the enlarged initial winding 34 to achieve either form of such blocking lesion.

One skilled in the art will appreciate further features and advantages of the invention based on the above-described embodiments. Accordingly, the invention is not to be limited by what has been particularly shown and described, but will be seen to include further variations, modifications and adaptations within is scope, as defined by the claims appended hereto and equivalents thereof. All publications and references cited herein are expressly incorporated herein by reference in their entirety.

What is claimed is:

1. An ablative stent device comprising:

a self-expanding stent adapted to be implanted and deployed within a vessel to provide circumferential support of the vessel;

said stent including a proximal portion having a first diameter and an ablation region along at least a portion of its length, the ablation region being adapted for surface contact with the vessel and the ablation region subtending at least a substantially complete circumferential band and being effective to ablate a signal-blocking path within the vessel upon application of energy to the stent, the stent further including a distal portion having a second diameter that is less than the first diameter and that is sufficient to enable the stent to seat within the vessel.

2. The device of claim 1, wherein said ablation region comprises a winding at the proximal end of said stent.

3. A method of treating atrial fibrillation, such method comprising the steps of:

implanting in a pulmonary vein a stent including a proximal portion having a first diameter and an ablation region along at least a portion of its length, the ablation region being adapted for surface contact with the vessel and the ablation region subtending at least a substantially complete circumferential band and being effective to ablate a signal-blocking path within the vessel upon application of energy to the stent, the stent further including a distal portion having a second diameter that is less than the first diameter and that is sufficient to enable the stent to seat within the vessel, and energizing at least a portion of the stent to ablate a blocking lesion proximate the os.

4. The method of claim 3, wherein said portion is positioned to ablate a circumferential blocking lesion of the pulmonary vein wall.

5. The method of claim 3, wherein said portion is positioned to ablate a blocking lesion in posterior left atrium endocardial surface tissue substantially surrounding the os.

6. A stent device, comprising:

a self-expanding, implantable stent having a proximal portion with a first diameter and a conductive, ablation region along at least a portion of its length and adapted to contact adjacent tissue, the ablation region subtending at least a substantially complete circumferential band and being effective to ablate a signal blocking path within the tissue upon application of energy to the ablation region, the stent further including a distal portion having a second diameter that is less than the first diameter and that is sufficient to enable the stent to seat within the vessel.

* * * * *